US009284592B2

(12) United States Patent
Oehrle

(10) Patent No.: US 9,284,592 B2
(45) Date of Patent: Mar. 15, 2016

(54) METHODS FOR THE DETERMINING THE PRESENCE OR ABSENCE OF CYANOBACTERIA TOXINS

(75) Inventor: Stuart A. Oehrle, Cold Spring, KY (US)

(73) Assignee: Waters Technologies Corporation, Milford, MA (US)

( * ) Notice: Subject to any disclaimer, the term of this patent is extended or adjusted under 35 U.S.C. 154(b) by 1163 days.

(21) Appl. No.: 13/126,311

(22) PCT Filed: Oct. 28, 2009

(86) PCT No.: PCT/US2009/062299

§ 371 (c)(1), (2), (4) Date: Jun. 17, 2011

(87) PCT Pub. No.: WO2010/051295

PCT Pub. Date: May 6, 2010

(65) Prior Publication Data

US 2011/0269241 A1 Nov. 3, 2011

Related U.S. Application Data

(60) Provisional application No. 61/110,021, filed on Oct. 31, 2008.

(51) Int. Cl.

| | |
|---|---|
| ***G01N 30/08*** | (2006.01) |
| ***G01N 30/96*** | (2006.01) |
| ***G01N 1/40*** | (2006.01) |
| ***C12Q 1/04*** | (2006.01) |
| ***G01N 33/50*** | (2006.01) |
| ***G01N 33/68*** | (2006.01) |

(Continued)

(52) U.S. Cl.

CPC .................. *C12Q 1/04* (2013.01); *G01N 30/08* (2013.01); *G01N 30/96* (2013.01); *G01N 33/50* (2013.01); *G01N 33/6848* (2013.01); *B01J 39/046* (2013.01); *B01J 41/046* (2013.01); *G01N 1/40* (2013.01); *G01N 2333/195* (2013.01); *Y10T 436/17* (2015.01)

(58) Field of Classification Search

None

See application file for complete search history.

(56) References Cited

U.S. PATENT DOCUMENTS

| | | | | |
|---|---|---|---|---|
| 6,730,517 | B1 | 5/2004 | Koster et al. | |
| 2006/0096925 | A1 * | 5/2006 | Roffman et al. | 210/660 |

(Continued)

FOREIGN PATENT DOCUMENTS

| | | | |
|---|---|---|---|
| CN | 101454666 | A | 6/2009 |
| EP | 1182439 | A | 4/2011 |

(Continued)

OTHER PUBLICATIONS

Kungsuwan, A. et al. "Isolation of Two Toxins from the Blue-green Alga Microcystis aeruginosa," Nippon Suisan Gakkaishi 53(11), 2051-2054 (1987).*

(Continued)

*Primary Examiner* — Yelena G Gakh
*Assistant Examiner* — Michelle Adams
(74) *Attorney, Agent, or Firm* — Waters Technologies Corporation

(57) ABSTRACT

Kits and methods for the detection of toxins produced by cyanobacteria are disclosed. The methods include preparing a sample that potentially includes cyanobacterial toxins on a solid phase extraction device. In some embodiments, the sample extract can be formed using a weak cationic exchange process and a weak anionic exchange process.

18 Claims, 3 Drawing Sheets

(51) Int. Cl.
*B01J 39/04* (2006.01)
*B01J 41/04* (2006.01)

(56) References Cited

U.S. PATENT DOCUMENTS

| | | | |
|---|---|---|---|
| 2006/0246225 | A1 | 11/2006 | Moritz et al. |
| 2008/0169242 | A1 | 7/2008 | Lu et al. |

FOREIGN PATENT DOCUMENTS

| | | | |
|---|---|---|---|
| JP | 3768442 | B2 | 4/2006 |
| WO | 0060361 | A3 | 10/2000 |

OTHER PUBLICATIONS

James, K. J. et al. "Sensitive determination of anatoxin-a, homoanatoxin-a and their degradation products by liquid chromatography with fluorimetric detection," Journal of Chromatography A, 798 (1998) 147-157.*

"Purity by SPE: Oasis® Sample Extraction Products," Waters Corporation, 2006.*

Gerssen, A. et al. "Solid phase extraction for removal of matrix effects in lipophilic marine toxin analysis by liquid chromatography-tandem mass spectrometry," Anal Bioanal Chem (2009) 394:1213-1226; Published online: Apr. 24, 2009.*

Kubo et al.; "Effective determination method for a cyanobacterial neurotoxin, b-N-methylamino-l-alanine" Toxicon 51 (2008) 1264-1268.

Furey et al.; "The first identification of the rare cyanobacterial toxin, homoanatoxin-a, in Ireland", Toxicon 41 (2003) 297-303.

Kikuchi et al.; "Cylindrospermospin determination using 2-[4-1-hydroxyethyl)-1-piperazinyl]ethanesulfonic acid (HEPES) as the internal standard,", Analytica Chemica Acta 583 (2007) 124-127.

Meriluoto et al.; "Chromatography of microcystins", Analytica Chimica Acts 352 (1997) 277-298.

Waters Corp,The Science of What's Possible; "Acquity UPLC BEYH Column", Care and Use Manual, Jul. 2012, 12 pages.

Xu et al.; "Development and application of ultra performance liquid chromatography-electrospray ionizaiton tandem triple quadrupole mass spectgrometry for determination of seven microcystins in water sample", Analytica Chimica Acta, 616 (2008) 28-36.

Oehrle et al.; "Analysis of Various Cyanobacterial Toxins by LC-MS", LCGC North America, vol. 21, No. 7, Jul. 2003, www.chromatographyonline.com.

European Search Report for application No. 09824083.1, dated May 14, 2013, 10 pages.

Oehrle, et al.; Detection of Various Freshwater Cyanobacterial Toxins using Ultra-Performance Liquid Chromatography-Tandem Mass Spectrometry, Toxicon 55 (2010) p. 965-972, www.elsevier.com/locate/toxicon.

Wang, et al.; An ultra-performance liquid chromatography-tandem mass spectrometry method for determination of microcystins occurrence in surface water in Zhejiang Province, China, Toxicon 49 (2007) p. 1120-1128, www.elsevier.com/locate/toxicon.

Gritti, et al.; Ultra high pressure liquid chromatography. Column permeability and changes of the eluent properties, J. Chromatogr A. Apr. 11, 2008, 1187 (1-2): 165-79, Epub Feb. 15, 2008, abstract only.

Liming Cong, et al.; "Determination of Trace Amount of Microcystins in Water Samples Using Liquid chromatography Coupled with Triple Quadrupole Mass Spectrometry," Analytica Chimica Acta 569 (2006) 157-168.

* cited by examiner

1=CYLINDROSPERMOPSIN, 2=ANATOXIN-a, 3=CYCLO (Arg-Ala-Asp-D-Phe-Val) (Std), 4=$[Leu^5]$-ENKEPHALIN (Std), 5=MICROCYSTIN RR, 6=NODULARIN, 7=MICROCYSTIN YR, 8=MICROCYSTIN LR, 9=MICROCYSTIN LA, 10=MICROCYSTIN LY, 11=MICROCYSTIN LW, AND 12=MICROCYSTIN LF

METHODS FOR THE DETERMINING THE PRESENCE OR ABSENCE OF CYANOBACTERIA TOXINS

CROSS-REFERENCE TO RELATED APPLICATIONS

This application is the National Stage of International Application No. PCT/US2009/062299, filed Oct. 28, 2009, filed on and designating the United States, which claims benefit of a priority to U.S. Provisional Patent Application No. 61/110,021, filed Oct. 31, 2008. The contents of these applications are expressly incorporated herein by reference in its entirety.

STATEMENT REGARDING FEDERALLY SPONSORED RESEARCH OR DEVELOPMENT

The inventions of the present application were not made with Federal or state funds or grants.

THE NAMES OF THE PARTIES TO A JOINT RESEARCH AGREEMENT

The inventions of the present application were not made under a joint research agreement.

REFERENCE TO SEQUENCE LISTING

The present application does not have any nucleic acid, peptide or protein sequence.

BACKGROUND OF THE INVENTION

Embodiments of the present invention are directed to kits and methods for the detection of toxins produced by cyanobacteria. Cyanobacteria are commonly found in surface fresh water. Toxic cyanobacteria blooms are problems where such blooms may cause toxins to be released in water supplies. The major cyanobacterial toxins comprise cyclic peptides, alkaloids and lipopolysaccharides.

By way of example, without limitation, the major cyclic peptides comprising cyanobacterial toxins are nodulin, microcystin-LR, microcystin RR, and microcystin YR. The formula for nodulin is set forth below:

Formula 1

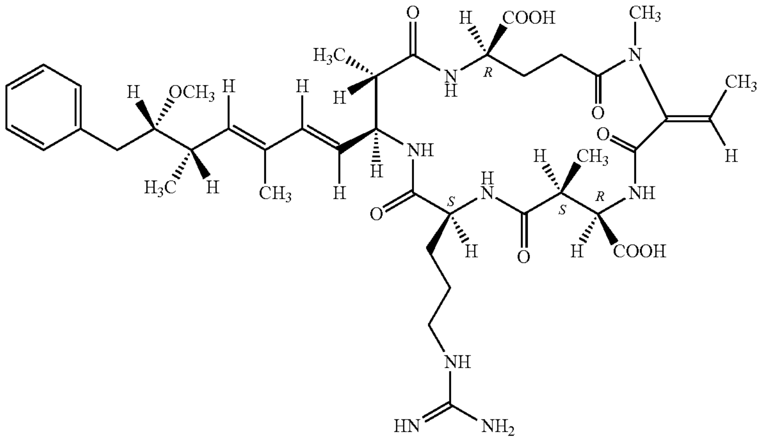

The formula for microcystin LR is set forth below:

Formula 2

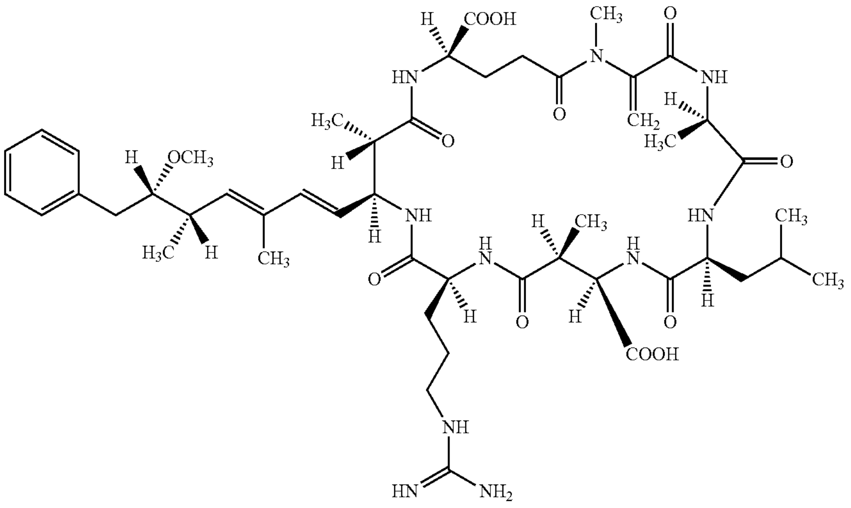

The formula for microcystin RR is set forth below:
Formula 3
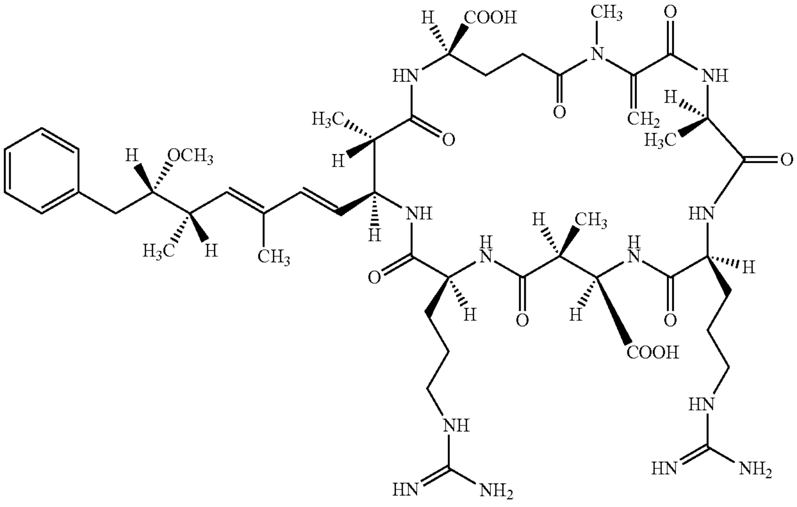
The formula for microcystin YR is set forth below:
Formula 4
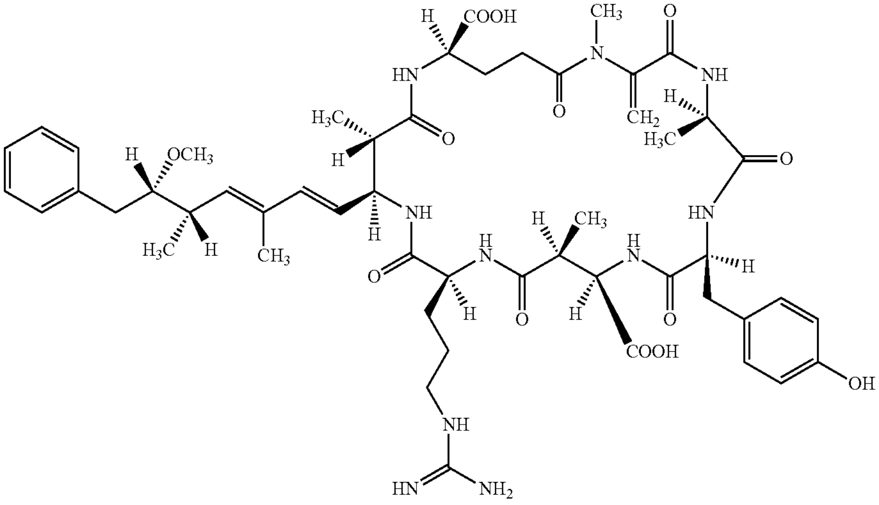
The formula for microcystin LA is set forth below:
Formula 5
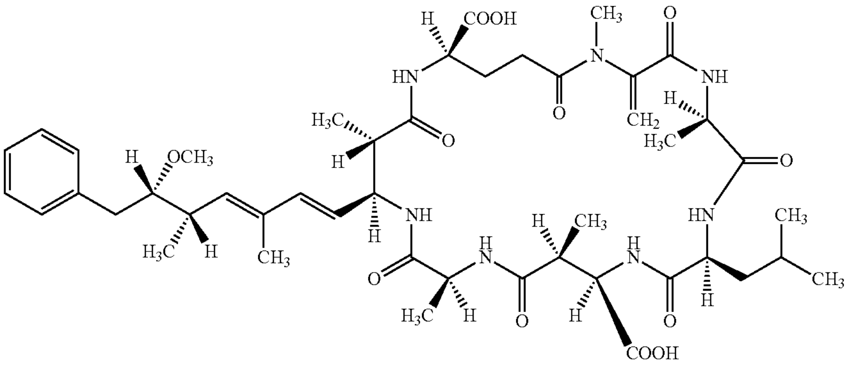

The formula for microcystin LY is set forth below:
Formula 6
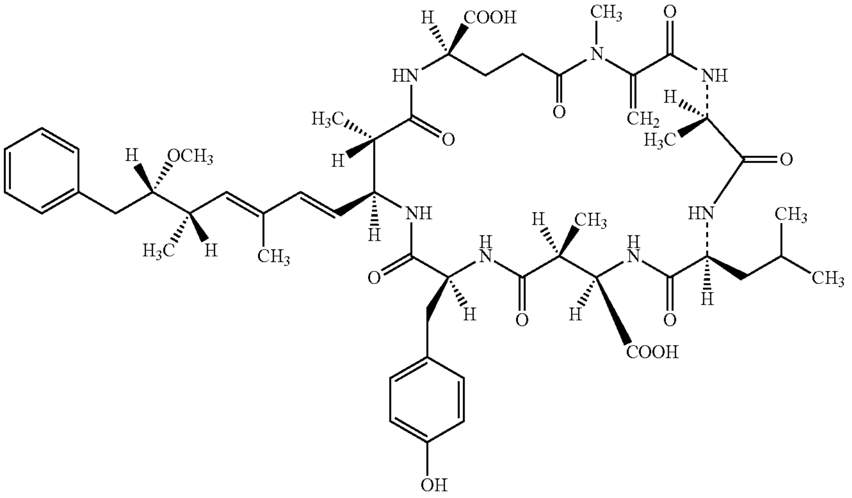
The formula for microcystin LW is set forth below:
Formula 7
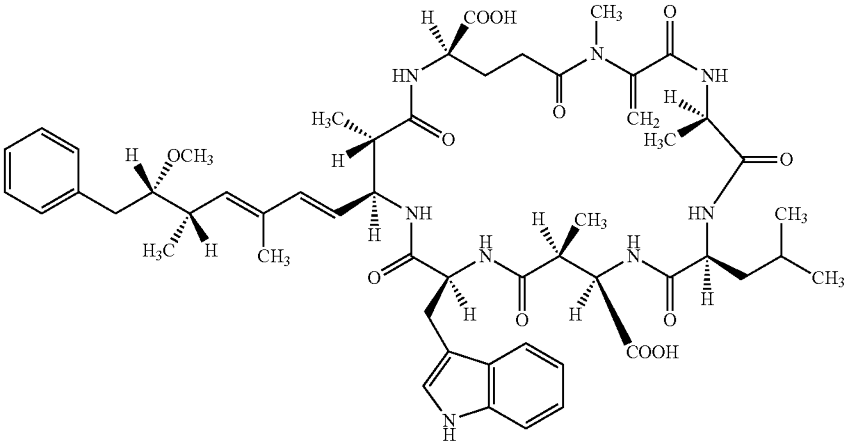
LW
MW = 1025.
The formula for microcystin LF is set forth below:
Formula 8
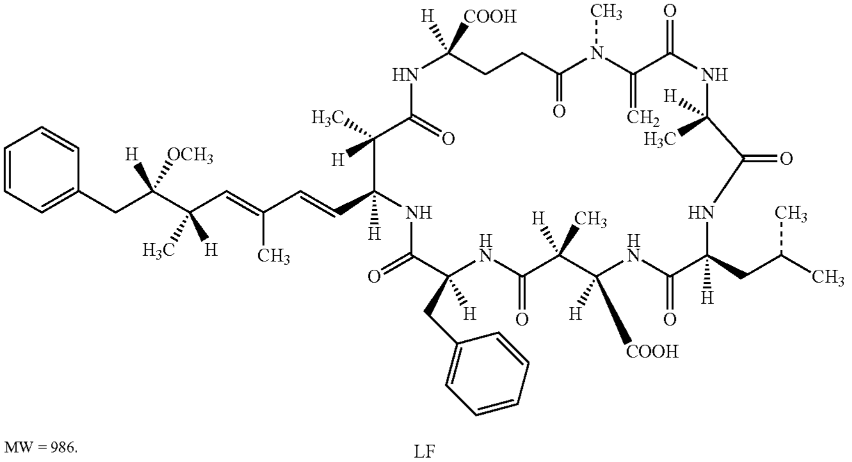
MW = 986.
LF The alkaloid cyanobacterial toxins comprise, by way of example, without limitation, anaroxins and saxitoxins. Anaroxins comprise, by way of example, without limitation, anatoxin a, anatoxin a(S), homoanatoxin-a, cylindrospermopsin.

The formula for anatoxin a is set forth below:

FIG. Chemical structures of anatoxins. Anatoxin-a, homoanatoxin-a, and anatoxin-a(s).

Formula 9, 10, 11

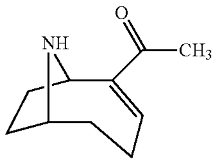

ANATOXIN-a

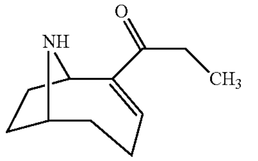

HOMOANATOXIN-a

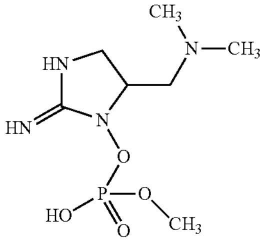

ANATOXIN-a(s)

The formula for cylindrospermopsin is set forth below:

Formula 12

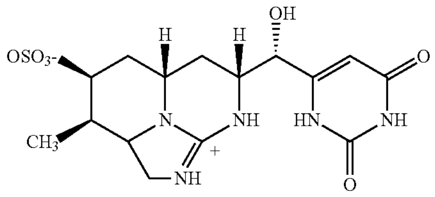

The cyanobacterial lipopolysaccharides toxins are not as well characterized and appear to be less toxic than the cyclic peptides, alkaloids.

This paper will use the term "analyte" to denote a compound which one desires to determine the presence of absence of.

This paper will use the term "sample" to mean a material which one desires to test for the presence or absence of ergot alkaloids. The sample may be obtained as tissues or fluids from animals or plants. For example, without limitation, the sample may comprise leaves, seeds or other plant tissues or blood, urine, saliva or tissues obtained from animal sources.

An "extract" is a solution obtained by subjecting a sample to a solvent such that one or more compounds held in the sample are dissolved in the solution.

An "aliquot" is used to denote a subpart or fraction of a sample.

Chromatography is a method of separating compounds in a solution. Chromatography can be performed in different devices. This paper will use the term "cartridge" to refer to low pressure devices comprising a column and/or funnel in which a solid phase is placed. The sample is applied to the solid phase and passes through under low pressure or gravity. These devices are typically used to prepare a sample by removing particulates and concentrating desired compounds.

For the purpose of this paper, the term "column" will be used in the sense of a high pressure device in which solutions are forced through a solid phase matrix under pressure. The solid phase can be particulate or a porous monolith.

Mass spectrometry is used to determine the mass to charge ratio of ions formed by compounds. Mass spectrometers are used to form fragments of larger molecules and such fragments and complete ions are used to identify such compounds.

Standards are solutions with known amounts of compounds which solutions are used to compare data to data derived from non-standard samples. Standards can use compounds with labels comprising heavy isotopes which allow the operator of the mass spectrometer to differentiate between the standard and the analyte.

Interest in reliable and fast analysis of cyanobacterial toxins is needed to monitor water supplies, protect public health and fisheries. Prior to the present invention, the methods used to detect cyanobacterial toxins were not specific or sensitive to analyze for these compounds in the environment. Prior to the present invention, the methods were time consuming and labor intensive.

BRIEF SUMMARY OF THE INVENTION

Embodiments of the present invention are directed to reliable and fast analysis of cyanobacterial toxins. Embodiments of the present invention have utility for monitoring water supplies, protecting public health and fisheries. Embodiments of the present invention are directed to methods and kits for the detection of cyanobacterial toxins.

One embodiment of the present invention, directed to a method for detecting the presence or absence of cyanobacterial toxins in a sample comprises the steps of preparing a water sample potentially comprising cyanobacterial toxins to form a retained or concentrated toxin sample on a solid phase extraction device. Next, the retained or concentrated toxin sample is eluted in a mobile phase to form a sample extract. The sample extract is placed on the head of a chromatographic column packed with particles having a mean particle size of 1 to 3 microns under pressure of 6,000 to 15,000 psi to form a retained sample potentially comprising cyanobacterial toxin, in the event said sample extract contained such cyanobacterial toxins. Compounds from said retained sample, potentially comprising cyanobacterial toxins, are eluted from said chromatographic column under a gradient of organic solvent to form at least one eluted compound. This eluted compound comprises a cyanobacterial toxin, in the event said sample extract contained such cyanobacterial toxin. And, the eluted compound, potentially comprising a cyanobacterial toxin, is placed in a mass spectrometer to form a mass spectra. The mass spectra are used to determine the presence or absence of the cyanobacterial toxin.

Embodiments of the present method can be performed from said steps of placing the sample extract on the head of a chromatographic column to eluting and placing said cyanobacterial toxin in a mass spectrometer in a time period of less than fifteen minute and, preferably, ten minutes.

Preferably, the mass spectrometer forms one or more fragments of the cyanobacterial toxin and the spectra of the fragments are used to identify and determine the presence or absence of the cyanobacterial toxin. Preferably, the method comprises comparing the spectra from the parent ions and fragments to those obtained with standards.

Preferably, the column has a particle is selected from the group consisting of a bridged ethyl hybrid and high strength silica. Preferred particles have a mean average diameter of less than three microns.

Preferably, the sample extract is formed by extracting alkaloid cyanobacterial toxins on weak anion exchange resin. Preferably, the sample extract is formed by extracting cyclic peptide cyanobacterial toxins on weak cation exchange resin. The sample extract is preferably formed with an extraction cartridge or extraction device having a weak anion exchange resin or a weak cation exchange resin. Most preferably, the method comprises the step of forming at least one sample extract with both a weak cation exchange resin and a weak anion exchange resin. A preferred resin capable of being functionalized with weak anionic and weak cationic functional groups comprising a polymer, poly(divinylbenzene-co-N-vinylpyrrolidone).

A further embodiment of the present invention is directed to a kit for performing an analysis of a sample for the presence or absence of cyanobacterial toxins. As used herein, the term "kit" refers to an article of manufacture, an assembly of parts, reagents, and components for performing a method. Kits are typically packaged in suitable packaging such a wrap, box, clam shell or bag with instructions for use. Embodiments of the present invention comprise one or more standards for calibrating and facilitating the identification of one or more cyanobacterial toxins by mass spectroscopy. The kit, preferably, comprises sample preparation devices for forming sample extract, a column for separating the compounds of the sample extract and upon application of a gradient releasing the cyanobacterial toxins, if present, such that the cyanobacterial toxins are released to a mass spectrometer for identification.

A preferred column has a packing of particles having an average size of 1-3 microns. A preferred particle has a chromatographic surface selected from the group consisting of a bridged ethyl hybrid and high strength silica. A preferred column has an operating pressure of 6,000 to 15,000 psi.

Other features and advantages of the present invention will be apparent to individuals skilled in the arts upon viewing the figures and the detailed description that follow.

DETAILED DESCRIPTION OF THE INVENTION

Embodiments of the present invention will be described in detail as methods and kits for the detection of cyanobacterial toxins. Embodiments of the present invention have utility for monitoring water supplies, protecting public health and fisheries, as well as food testing. The descriptions that follow are preferred embodiments reflecting what the inventors now consider is the best mode to practice their invention. Such descriptions are capable of modification and alteration by those skilled in the art without departing from the teaching hereof.

Figure 1:
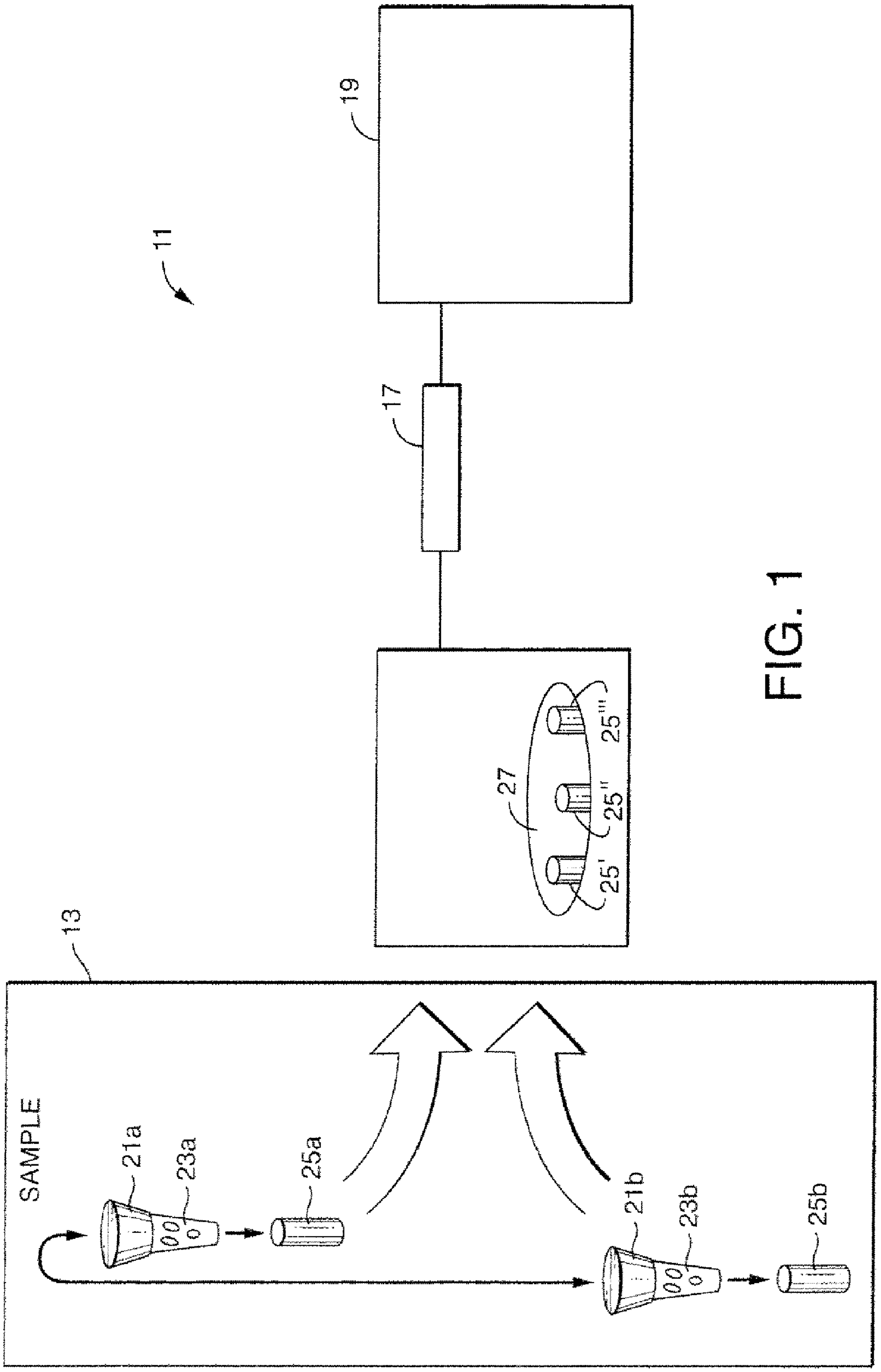
FIG. 1 depicts in schematic form an instrument for performing the method of the present invention.

One embodiment of the present invention, directed to a method for detecting the presence or absence of cyanobacterial toxins in a sample is depicted in schematic form in FIG. 1 with respect to an instrument generally designated by the numeral 11. The instrument, generally designated by the numeral 11, has the following major elements: sample preparation means 13, a chromatography system 15, a column 17 and a mass spectrometer 19.

The method comprises the step of preparing a water sample potentially comprising cyanobacterial toxins with respect to sample preparation means 13. As depicted, sample preparation means 13 comprises at least one sample extraction cartridge 21*a* and, preferably two sample extraction cartridges 21*a* and 21*b*.

Sample extraction cartridges 21*a* and 21*b* are depicted in cross section. Each sample extraction cartridge 21*a* and 21*b* has a solid phase 23*a* and 23*b*. A solid phase may comprise a bed of particles or a porous monolith resin. A preferred solid phase is particular and has a surface chemistry of poly(divinylbenzene-co-N-vinylpyrrolidone). That is, the particles may totally comprise the polymer or such polymer is carries as a surface layer on a substrate that is selected from a different material. Common materials which may be used as a substrate include, by way of example, without limitation, silica, aluminium and titanium oxides and other polymeric compounds. The surface chemistry of poly(divinylbenzene-co-N-vinylpyrrolidone) allows the particles of the sample extraction column to retain cyanobacterial toxins on a water wettable surface or allow the surface to be functionalized in a manner to capture cyanobacterial toxins more selectively or efficiently.

Sample extraction cartridges having a surface chemistry of poly(divinylbenzene-co-N-vinylpyrrolidone) are sold by Waters Corporation (Milford, Mass., USA) under the trademark OASIS®. Sample extraction cartridges without a surface chemistry of poly(divinylbenzene-co-N-vinylpyrrolidone) may also be used. Such sample extraction cartridges are sold by Waters Corporation (Milford, Mass., USA) under the trademark SEP-PAK.

Particles having a surface functionalized are preferably functionalized as weak cation exchange resins and or weak anion exchange resins for the preferential or efficient capture of cyanobacterial toxins. For example, without limitation, the sample extract is formed by extracting on weak anion exchange resin to favor alkaloid cyanobacterial toxins and formed on weak cation exchange resins to favor cyclic peptide cyanobacterial toxins.

Thus, as depicted, the sample is divided into two or more parts with one part directed to a first sample extraction cartridge 21*a* having a particle bed 23*a* comprising a weak anion exchange resin to favor alkaloid cyanobacterial toxins. A second sample extraction cartridge 21*b* has a particle bed 23*b* comprising a weak cation exchange resin to favor cyclic peptide cyanobacterial toxins. Such sample extraction cartridges 21*a* and 21*b* having weak cation or weak anion exchange resins are sold by several vendors including those sold by Waters Corporation (Milford, Mass.) under the trademark OASIS® WCX and OASIS® WAX.

The sample preparation means is depicted as sample extraction cartridges 21*a* and 21*b* as single well type devices with the understanding that such devices may have many forms comprising, by way of example, without limitation, single columns, cartridges and well devices as well as multiple well devices, such as 96 well plates and the like.

Most preferably, the method comprises the step of forming at least one sample extract with both a weak cation exchange resin and a weak anion exchange resin. The sample extract from sample extraction cartridge 21*a* is eluted and placed in a vial 25*a* and the sample extract from sample extraction cartridge 21*b* is eluted placed in vial 25*b*. The sample extraction cartridges 21*a* and 21*b* retain the cyanobacterial toxin and release the cyanobacterial toxin upon elution with a mobile phase in a more concentrated form. This sample extract is placed and held in vials 25*a* and 25*b*.

The vials 25*a* and 25*b* are placed in a chromatography system 15 autosampler, depicted in schematic form as a circular tray 27 holding vials 25', 25", and 25'". Chromatography systems are well known in the art. A preferred chromatography system 15 has an operating pressure of 6,000 to 15,000 psi. Such chromatography systems 15 are sold by Waters Corporation (Milford, Mass., USA) under the trademark ACQUITY®.

Figure 2:
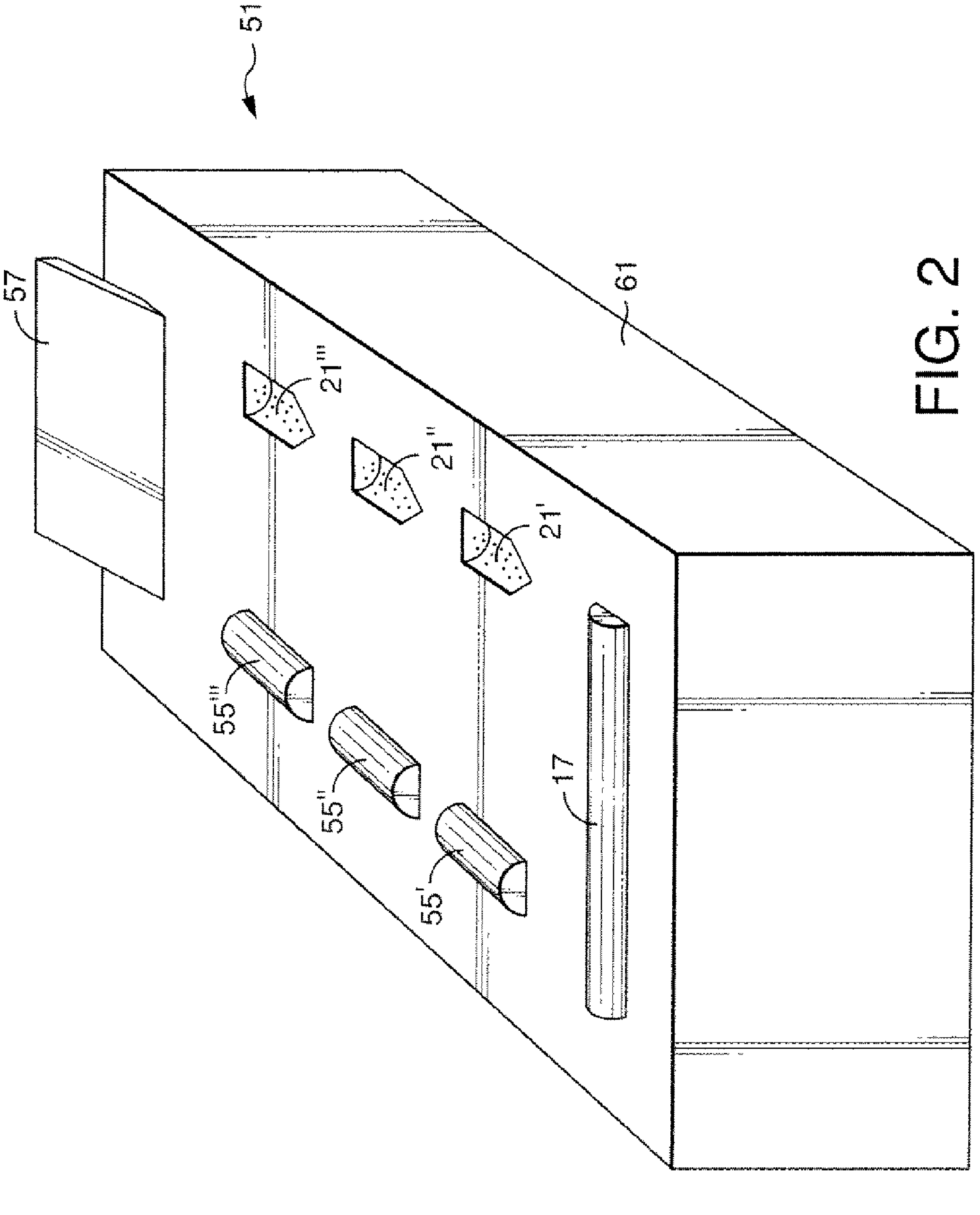
FIG. 2 depicts a kit embodying features of the present invention.

Next, as depicted in FIG. 2, the method comprises the step of placing the sample extract on the head of chromatographic column 17. Chromatographic column 17 is packed with particles having a mean particle size of 1 to 3 microns. Chromatographic column 17 has an operating pressure of 6,000 to 15,000 psi. A preferred column has particles with a chromatographic surface of a bridged ethyl hybrid composition or a high strength silica. columns 17, having a 1.7 micron particle size, are sold by Waters Corporation (Milford, Mass., USA) under the trademark ACQUITY® with a BEH designation with respect to a bridged ethyl hybrid chemistry and a HSS designation with respect to high strength silica chemistry. In the event the sample extract held in vials 25', 25" or 25'" has one or more cyanobacterial toxin, a retained cyanobacterial toxin is held on the particles until eluted under gradient conditions. The compounds of the sample are retained on the column to form one or more retained compounds.

Next, the one or more retained compounds are eluted under a gradient of organic solvent to form an eluted compound. And, in the event said sample extract contained such cyanobacterial toxins, such eluted compound is a toxin. A preferred gradient comprises a first solvent comprising 0.1% Formic Acid ($H_2O$) and a second solvent comprising 0.1% Formic Acid (acetonitrile). The gradient is applied at a flow rate of 0.1 to 1.0 ml/min, and more preferably, at about 0.45 ml/min over a period of approximately six minutes moving from 2% of the first solvent to 80% of the second solvent.

This eluted cyanobacterial toxin, if present, is placed in a mass spectrometer 19 to form a mass spectra. The presence or absence of the cyanobacterial toxin is determined from the mass spectra.

Preferably, the mass spectrometer 19 forms one or more fragments of the cyanobacterial toxin. The formation of fragments in mass spectroscopy is sometimes denoted as MS/MS and is known to those skilled in the art. The spectra of the fragments are used to identify and determine the presence or absence of an cyanobacterial toxin. Mass spectrometers are sold by several venders including Waters Corporation (Milford, Mass., USA) under the trademark MICROMASS® TQD.

The identification of the cyanobacterial toxin, if present, is facilitated by placing one or more standards comprising a known labeled cyanobacterial toxin or closely related compound on the head of a column to be retained and eluted in the manner of sample cyanobacterial toxin. The eluted standard cyanobacterial toxin is placed in a mass spectrometer 19 to form a known spectra of the standard cyanobacterial toxin to which sample spectra are compared. Such labeled cyanobacterial toxin or closely related compound is used in a deuterated form known to individuals skilled in the art. The examples feature Cyclo (Arg-Ala-Asp-D-Phe-Val) and [Leu5]-Enkephalin.

The small particle column and high pressure performance of the chromatography system allow the method steps of placing the sample extract on the head of a chromatographic column, eluting and placing the cyanobacterial toxin in a mass spectrometer to be performed in a time period of three to fifteen minutes, and routinely in a period of approximately eight to nine minutes.

Preferably, the mass spectrometer forms one or more fragments of the cyanobacterial toxin and the spectra of the fragments are used to identify and determine the presence or absence of the cyanobacterial toxin. Preferably, the method comprises comparing the spectra from the parent ions and fragments to those obtained with standards.

Turning now to FIG. 2, a kit embodying features of the present invention, generally designated by the numeral 51, is illustrated. The kit is a collection of parts and reagents bundled together with suitable packaging and instructions for their use in the method described above. Kit 51 comprises one or more standard vials, of which three are depicted designated 55', 55" and 55'", containing standard solutions for calibrating and facilitating the identification of one or more cyanobacterial toxins by mass spectroscopy. The kit 51 further comprises one or sample preparation devices in the form of extraction cartridges, of which three are depicted 21', 21", and 21'" for forming sample extract. The kit further comprises a column 17 for separating the compounds of the sample extract and upon application of a gradient releasing the cyanobacterial toxins, if present, such that the cyanobacterial toxins are released to a mass spectrometer for identification. The kit 51 further comprises instructions 57 for the use of these parts and reagents in the method as previously described. The kit is depicted with suitable packaging, which is known in the art, and may comprise plastic wraps and bubble shells, boxes, wrapping and the like.

Further features of the present invention are described with respect to the following examples.

Example 1

Multi Column Solid Phase Extraction (SPE) Using Mixed Mode Cartridges

This discussion is focused on an analysis of cylindrospermopsin, anatoxin-a and microcystins from lake or process water or water extracts from filters or other surfaces.

Method Summary:

Cartridges are initially conditioned, equilibrated and loaded in series (OASIS®WCX on top followed by OASIS® WAX cartridge with a union connecting the two). Once loaded they are separated and processed individually and run as two separate runs Protocol:

WAX (6 cc 150 mg Waters part number 186002493)—This is for cylindrospermopsin enrichment (this is on the bottom)

Condition: 3 mL MeOH

Equilibrate: 5 mL H2O

Load: Up to 500 mL of sample water (pH the water to pH 5.5 with formic acid)

Separate Columns and Continue on Each Separately

Wash: 2 mL 1% Formic in DI H2O

Wash 2: 2 mL MeOH

Elute: 3 mL 1% ammonium hydroxide in DI H2O

Run "as is" or evaporate to dryness and reconstitute in mobile phase

WCX (6 cc 150 mg Waters part number 186002498)—This is for anatoxin-a, and microcystins enrichment (this is on the top)

Condition: 3 mL MeOH

Equilibrate: 5 mL H2O

Load: Up to 500 mL of sample water (pH the water to pH 5.5 with formic acid)

Separate Columns and Continue on Each Separately

Wash: 2 mL pH 9 ammonium hydroxide or ammonium bicarbonate in DI H2O

Wash 2: 2 mL MeOH

Elute: 3 mL 1% Formic acid in DI H2O

These cartridges are run "as is" or evaporated to dryness and reconstituted in mobile phase.

Example 2

Anatoxin-a, Cylindrospermopsin, and Microcystins by Extreme Pressure High Performance Liquid Chromatography/MS/MS This example features the separation and mass spectral analysis of anatoxin-a, cylindrospermopsin, and several microcystins by high performance liquid chromatography and mass spectrometry.

Column Used: HSS T3 2.1×100 mm @35 C

OR BEH C18 2.1×100 mm @35 C

Solvent A: 0.1% Formic Acid in H2O

Solvent B: 0.1% Formic in Acid in Acetonitrile

[Gradient Table]

| Time (min) | Flow Rate | % A | % B | Curve |
|---|---|---|---|---|
| Initial | 0.450 | 98.0 | 2.0 | — |
| 0.80 | 0.450 | 98.0 | 2.0 | 6 |
| 9.00 | 0.450 | 30.0 | 70.0 | 6 |
| 9.05 | 0.450 | 20.0 | 80.0 | 6 |
| 9.90 | 0.450 | 20.0 | 80.0 | 6 |
| 9.91 | 0.450 | 98.0 | 2.0 | 6 |
| 12.00 | 0.450 | 98.0 | 2.0 | 6 |

Figure 3:
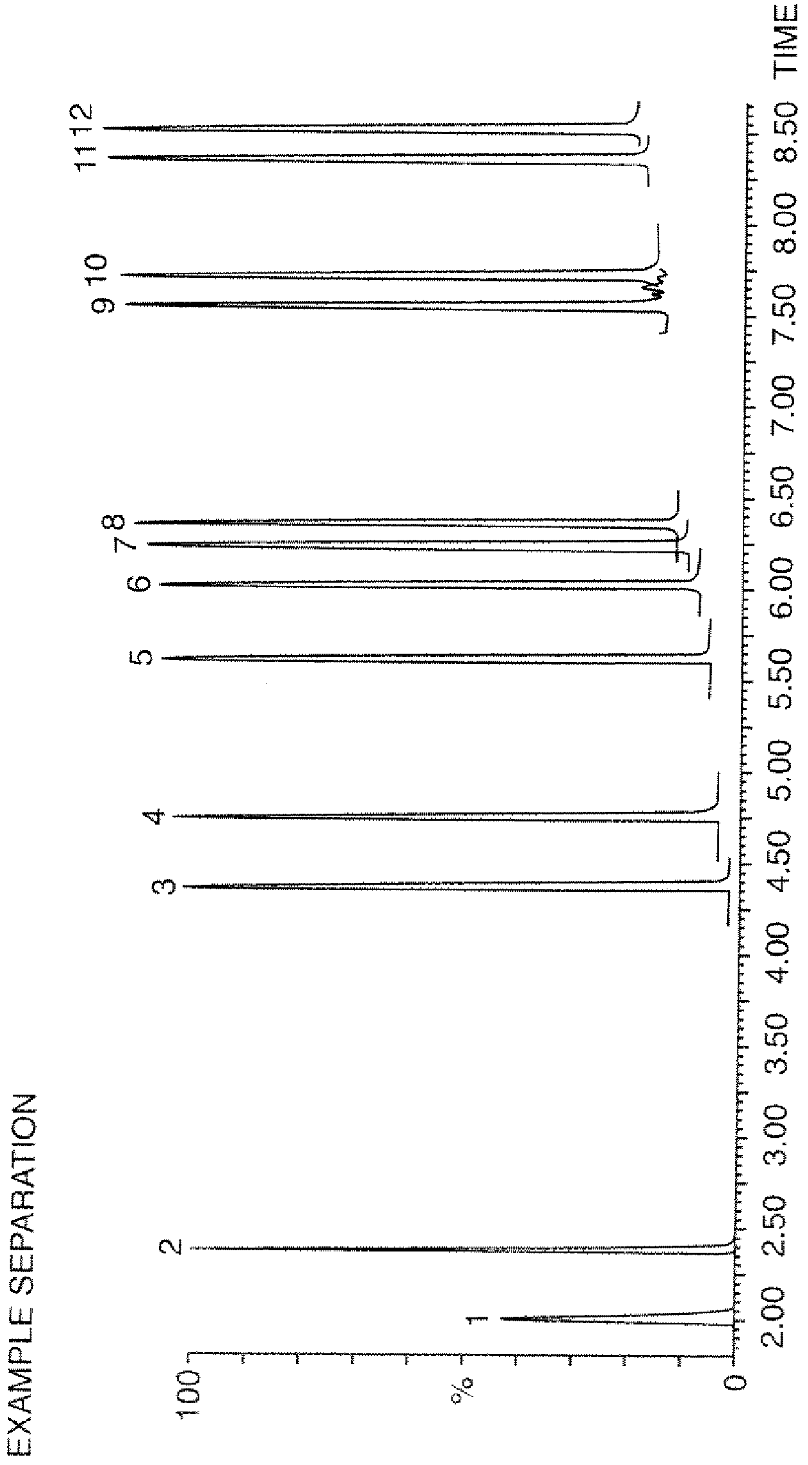
FIG. 3 depicts a separation and mass chromatogram of cyanobacterial toxins.

These results are set forth in FIG. 3. These results suggest that the compounds identified can be separated and identified in less than nine minutes.

TQD Conditions (MS/MS)

Function 1—Cylindrospermopsin

Retention window (mins): 1.000 to 2.220

Ionization mode: ES+

Data type: MRM data

Function type: MRM of 3 channels

| Chan Reaction | Dwell (secs) | Cone Volt. | Col. Energy | Delay (secs) | Compound |
|---|---|---|---|---|---|
| 1: 416.20 > 176.23 | 0.060 | 45.0 | 39.0 | Auto | Cylindro (C1) |
| 2: 416.20 > 194.25 | 0.060 | 45.0 | 37.0 | Auto | Cylindro (Q) |
| 3: 416.20 > 416.20 | 0.060 | 45.0 | 5.0 | Auto | Cylindro (C2) |

Function 2—Anatoxin-a

Retention window (mins): 2.220 to 3.000

Ionization mode: ES+

Data type: MRM data

Function type: MRM of 3 channels

| Chan Reaction | Dwell (secs) | Cone Volt. | Col. Energy | Delay (secs) | Compound |
|---|---|---|---|---|---|
| 1: 166.13 > 43.03 | 0.060 | 20.0 | 23.0 | Auto | Anatoxin (Q) |
| 2: 166.13 > 149.14 | 0.060 | 20.0 | 15.0 | Auto | Anatoxin (C1) |
| 3: 166.13 > 166.13 | 0.060 | 25.0 | 5.0 | Auto | Anatoxin (C2) |

Function 3—Cyclo (Arg-Ala-Asp-D-Phe-Val)—Used as an Internal Standard

Retention window (mins): 4.150 to 4.550

Ionization mode: ES+

Data type: MRM data

Function type: MRM of 3 channels

| Chan Reaction | Dwell (secs) | Cone Volt. | Col. Energy | Delay (secs) | Compound |
|---|---|---|---|---|---|
| 1: 589.47 > 72.77 | 0.050 | 55.0 | 73.0 | Auto | Cyclo (IS)-C2 |
| 2: 589.47 > 120.16 | 0.050 | 55.0 | 57.0 | Auto | Cyclo (IS) |
| 3: 589.47 > 589.47 | 0.050 | 55.0 | 5.0 | Auto | Cyclo (IS)-C1 |

Function 4—=[Leu5]-Enkephalin (Used as an Internal Standard)

Retention window (mins): 4.500 to 5.000

Ionization mode: ES+

Data type: MRM data

Function type: MRM of 3 channels

| Chan Reaction | Dwell (secs) | Cone Volt. | Col. Energy | Delay (secs) | Compound |
|---|---|---|---|---|---|
| 1: 556.42 > 120.16 | 0.050 | 35.0 | 53.0 | Auto | Enk (IS)-C2 |
| 2: 556.42 > 136.17 | 0.050 | 35.0 | 53.0 | Auto | Enk (IS) |
| 3: 556.42 > 556.42 | 0.050 | 35.0 | 5.0 | Auto | Enk (IS)-C1 |

Function 5—Microcystin RR

Retention window (mins): 5.400 to 6.000

Ionization mode: ES+

Data type: MRM data

Function type: MRM of 3 channels

| Chan Reaction | Dwell (secs) | Cone Volt. | Col. Energy | Delay (secs) | Compound |
|---|---|---|---|---|---|
| 1: 519.99 > 135.10 | 0.070 | 45.0 | 32.0 | Auto | RR (Q) |
| 2: 519.99 > 519.99 | 0.070 | 45.0 | 5.0 | Auto | RR (C1) |
| 3: 1038.69 > 135.10 | 0.070 | 90.0 | 80.0 | Auto | RR (C2) |

Function 6—Microcystin YR

Retention window (mins): 6.100 to 6.400

Ionization mode: ES+

Data type: MRM data

Function type: MRM of 2 channels

| Chan Reaction | Dwell (secs) | Cone Volt. | Col. Energy | Delay (secs) | Compound |
|---|---|---|---|---|---|
| 1: 1045.60 > 135.18 | 0.050 | 95.0 | 50.0 | Auto | YR (Q) |
| 2: 1045.60 > 1045.60 | 0.050 | 95.0 | 5.0 | Auto | YR (C1) |

Function 7—Microcystin LR

Retention window (mins): 6.150 to 6.550

Ionization mode: ES+

Data type: MRM data

Function type: MRM of 2 channels

| Chan Reaction | Dwell (secs) | Cone Volt. | Col. Energy | Delay (secs) | Compound |
|---|---|---|---|---|---|
| 1: 995.66 > 135.11 | 0.050 | 85.0 | 50.0 | Auto | LR (Q) |
| 2: 995.66 > 995.66 | 0.050 | 50.0 | 5.0 | Auto | LR (C1) |

Function 8—Microcystin LA

Retention window (mins): 7.400 to 7.750
Ionization mode: ES+
Data type: MRM data
Function type: MRM of 2 channels

| Chan Reaction | Dwell (secs) | Cone Volt. | Col. Energy | Delay (secs) | Compound |
|---|---|---|---|---|---|
| 1: 910.57 > 135.11 | 0.050 | 45.0 | 50.0 | Auto | LA (Q) |
| 2: 910.57 > 910.57 | 0.050 | 45.0 | 5.0 | Auto | LA (C1) |

Function 9—Microcystin LY

Retention window (mins): 7.600 to 8.000
Ionization mode: ES+
Data type: MRM data
Function type: MRM of 2 channels

| Chan Reaction | Dwell (secs) | Cone Volt. | Col. Energy | Delay (secs) | Compound |
|---|---|---|---|---|---|
| 1: 1002.63 > 135.18 | 0.050 | 50.0 | 50.0 | Auto | LY (Q) |
| 2: 1002.63 > 1002.63 | 0.050 | 50.0 | 5.0 | Auto | LY (C) |

Function 10—Microcystin LW

Retention window (mins): 8.200 to 8.700
Ionization mode: ES+
Data type: MRM data
Function type: MRM of 2 channels

| Chan Reaction | Dwell (secs) | Cone Volt. | Col. Energy | Delay (secs) | Compound |
|---|---|---|---|---|---|
| 1: 1025.63 > 135.05 | 0.070 | 45.0 | 42.0 | Auto | LW (Q) |
| 2: 1025.63 > 1025.63 | 0.070 | 45.0 | 5.0 | Auto | LW (C1) |

Function 11—Microcystin LF

Retention window (mins): 8.430 to 8.700
Ionization mode: ES+
Data type: MRM data
Function type: MRM of 2 channels

| Chan Reaction | Dwell (secs) | Cone Volt. | Col. Energy | Delay (secs) | Compound |
|---|---|---|---|---|---|
| 1: 986.63 > 135.05 | 0.050 | 40.0 | 50.0 | Auto | LF (Q) |
| 2: 986.63 > | | | | | |

What is claimed:

1. A method of determining the presence or absence of cyanobacterial toxins in a sample comprising the steps of:

preparing, on a solid phase extraction device, a water sample potentially comprising one or more cyanobacterial toxins to form a retained or concentrated sample potentially comprising a toxin, the solid phase extraction device including a plurality of sample extraction cartridges, at least one of the plurality of sample extraction cartridges including a weak anion exchange resin and another at least one of the plurality of sample extraction cartridges including a weak cation exchange resin;

eluting or reconstituting, from said solid phase extraction device at low pressure or under gravity, said retained or concentrated toxin sample in a mobile phase to form a sample extract;

placing said sample extract on the head of a chromatographic column to form a retained sample potentially comprising the one or more cyanobacterial toxins in the event said sample extract contained such cyanobacterial toxins;

eluting compounds from said retained sample potentially comprising the one or more cyanobacterial toxins from said chromatographic column to form at least one eluted compound potentially comprising the one or more cyanobacterial toxins; and placing said at least one eluted compound potentially comprising the one or more cyanobacterial toxins in a mass spectrometer to form a mass spectrum and determining the presence or absence of said one or more cyanobacterial toxins from the mass spectrum.

2. The method of claim 1 wherein said mass spectrometer forms one or more fragments of the one or more cyanobacterial toxins and at least one spectrum of said fragments is used to identify and determine the presence or absence of said one or more cyanobacterial toxins.

3. The method of claim 1 wherein said steps of placing said sample extract on the head of a chromatographic column, eluting and placing said at least one eluted compound potentially comprising the one or more cyanobacterial toxins in a mass spectrometer are performed in a time period of less than fifteen minutes.

4. The method of claim 1 wherein the chromatographic column is packed with particles having a mean particle size of 1 to 3 microns under pressure of 6,000 to 15,000 psi.

5. The method of claim 4 wherein said particles have a mean average diameter of less than two microns.

6. The method of claim 4, wherein said particles are selected from the group consisting of bridged ethyl hybrid particles and high strength silica particles.

7. The method of claim 1 wherein said sample extract is formed by extracting alkaloid cyanobacterial toxins on weak anion exchange resin.

8. The method of claim 1 wherein said sample extract is formed by extracting cyclic peptide cyanobacterial toxins on weak cation exchange resin.

9. The method of claim 1 wherein said solid phase extraction device includes particles comprising a poly(divinylbenzene-co-N-vinylpyrrolidone) polymer.

10. The method of claim 1, wherein the sample extract is formed by extracting alkaloid cyanobacterial toxins on a weak anion exchange resin and extracting cyclic peptide cyanobacterial toxins on a weak cation exchange resin.

11. A method of determining the presence or absence of cyanobacterial toxins in a sample comprising the steps of:

preparing a sample potentially containing cyanobacterial toxins using a solid phase extraction comprising a weak anion exchange process and a weak cation exchange process thereby forming a sample extract, the solid phase extraction including elution of the sample extract at low pressure or under gravity using a solid phase extraction device including particles comprising a poly (divinylbenzene-co-N-vinylpyrrolidone) polymer;

passing the sample extract through a chromatographic column to form a retained sample potentially comprising cyanobacterial toxin;

eluting compounds from said retained sample from said chromatographic column to form at least one eluted compound potentially comprising a cyanobacterial toxin;

placing said eluted compound in a mass spectrometer to form a mass spectrum; and determining the presence or absence of the cyanobacterial toxin from the mass spectrum.

12. The method of claim 11, wherein the sample extract is formed by extracting alkaloid cyanobacterial toxins on a weak anion exchange resin and extracting cyclic peptide cyanobacterial toxins on a weak cation exchange resin.

13. A method of determining the presence or absence of cyanobacterial toxins in a sample comprising the steps of:

preparing, on a solid phase extraction device, a water sample potentially comprising one or more cyanobacterial toxins to form a retained or concentrated sample potentially comprising a toxin, the solid phase extraction device including a weak anion exchange resin and a weak cation exchange resin, wherein said solid phase extraction device includes particles comprising a poly (divinylbenzene-co-N-vinylpyrrolidone) polymer;

eluting or reconstituting, from said solid phase extraction device at low pressure or under gravity, said retained or concentrated toxin sample in a mobile phase to form a sample extract;

placing said sample extract on the head of a chromatographic column to form a retained sample potentially comprising the one or more cyanobacterial toxins in the event said sample extract contained such cyanobacterial toxins;

eluting compounds from said retained sample potentially comprising the one or more cyanobacterial toxins from said chromatographic column to form at least one eluted compound potentially comprising the one or more cyanobacterial toxins; and placing said at least one eluted compound potentially comprising the one or more cyanobacterial toxins in a mass spectrometer to form a mass spectrum and determining the presence or absence of said one or more cyanobacterial toxins from the mass spectrum.

14. The method of claim 13, wherein said solid phase extraction device comprises a plurality of sample extraction cartridges, at least one of the plurality of sample extraction cartridges including a weak anion exchange resin and another at least one of the plurality of sample extraction cartridges including a weak cation exchange resin.

15. The method of claim 13, wherein the chromatographic column is packed with particles having a mean particle size of 1 to 3 microns under pressure of 6,000 to 15,000 psi.

16. The method of claim 13 wherein said sample extract is formed by extracting alkaloid cyanobacterial toxins on weak anion exchange resin.

17. The method of claim 13 wherein said sample extract is formed by extracting cyclic peptide cyanobacterial toxins on weak cation exchange resin.

18. The method of claim 13, wherein the sample extract is formed by extracting alkaloid cyanobacterial toxins on a weak anion exchange resin and extracting cyclic peptide cyanobacterial toxins on a weak cation exchange resin.

* * * * *